United States Patent
Schaldach

(10) Patent No.: US 6,571,129 B2
(45) Date of Patent: May 27, 2003

(54) MEDICAL THERAPY APPARATUS AND SENSOR FOR ACQUIRING MOLECULAR-GENETIC INFORMATION FOR THE APPARATUS

(75) Inventor: Max Schaldach, Erlangen (DE)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 95 days.

(21) Appl. No.: 09/792,764

(22) Filed: Feb. 19, 2001

(65) Prior Publication Data

US 2002/0007199 A1 Jan. 17, 2002

(30) Foreign Application Priority Data

Feb. 19, 2000 (DE) .......................... 100 07 715

(51) Int. Cl.$^7$ ............................. A61N 1/18; A61N 1/365
(52) U.S. Cl. ......................................... 607/62; 600/309
(58) Field of Search ............ 607/1, 3, 62; 600/300–301, 600/308–310, 317, 322, 326, 329, 333

(56) References Cited

U.S. PATENT DOCUMENTS 6,354,298 B1 * 3/2002 Landfield et al. ............ 128/898
6,417,506 B1 * 7/2002 Pinkel et al. ................ 204/603

* cited by examiner

Primary Examiner—Jeffrey R. Jastrzab
(74) Attorney, Agent, or Firm—Hahn Loeser + Parks LLP; Stephen L. Grant

(57) ABSTRACT

The invention concerns a sensor for obtaining information about the state of an organism for a medical therapy apparatus, preferably for a therapy apparatus for the electrostimulation or other treatment of the heart. The invention is distinguished by at least one sensor element for detecting molecular-genetic information. The invention further concerns a medical therapy apparatus having a sensor of that kind.

15 Claims, 2 Drawing Sheets

Figure 1:
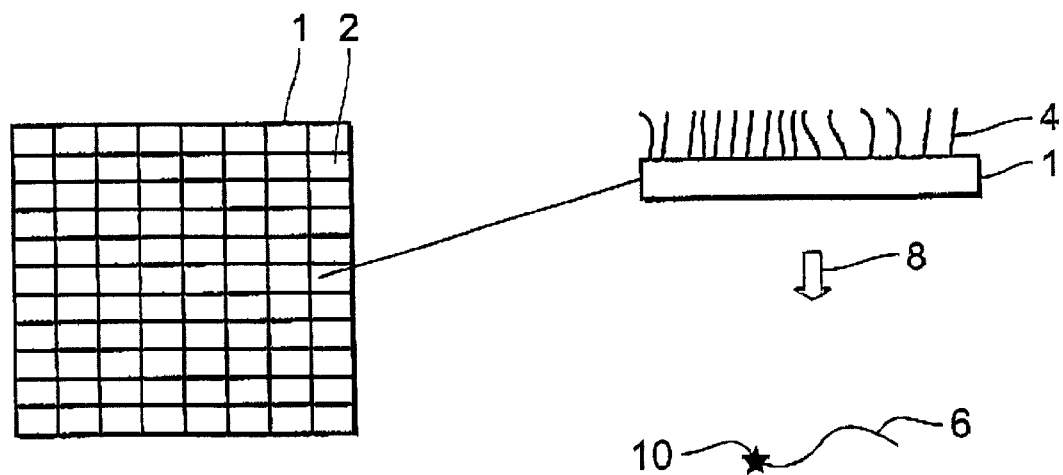

MEDICAL THERAPY APPARATUS AND SENSOR FOR ACQUIRING MOLECULAR-GENETIC INFORMATION FOR THE APPARATUS

The invention concerns a sensor for obtaining information about the state of an organism for a medical therapy apparatus, preferably for a therapy apparatus for the electrostimulation or other treatment of the heart.

Sensors of that kind are known from the state of the art. The items of information which are detected thereby are required by the medical therapy apparatuses in order to be able to operate in the optimum fashion. Thus for example sensors for therapy apparatuses for electrostimulation of the heart, in particular sensors for cardiac pacemakers or for defibrillators, detect cardiac disrhythmias, but sensors of electromedical apparatuses can also measure muscle activity, lung function parameters, oxygen saturation, blood pressure, hormone level or other physiological parameters. All those parameters can be used for controlling the pacemaker or the defibrillator.

In that respect, particularly in the case of cardiac pacemakers, it is important for the stimulation pulse produced by the pacemaker to be matched in terms of its stimulation amplitude to the stimulation threshold. The stimulation threshold characterises that stimulation amplitude of the pacemaker, which is required in order to trigger a stimulation outcome, that is to say a stimulated systole. As the stimulation threshold can vary as a consequence of hormone level, time of day, physical activity and so forth, it is advantageous if the stimulation amplitude can be adapted to that variation in the stimulation threshold. In that respect, the stimulation outcome itself can also be used for controlling the pacemaker. For, if for example the absence of a stimulation outcome after the delivery of a stimulation pulse (as a result of the absence of a rise in impedance in the impedance pattern after delivery of the stimulation pulse) means that a sub-threshold stimulation situation is detected by a suitable sensor, then the stimulation amplitude is to be increased in order to further ensure reliable functioning of the pacemaker. To sum up it can be noted that, in the case of electromedical therapy apparatuses, particularly in the case of cardiac pacemakers and defibrillators, optimisation of the function of the apparatus is all the more possible, the greater the number of parameters involved in control or regulation of the apparatus.

Therefore the object of the present invention is to so develop a sensor of the kind set forth in the opening part of this specification, that additional parameters which were hitherto not detected in the state of the art can be detected.

In a sensor of the kind set forth in the opening part of this specification, that object is attained in that there is provided at least one sensor element for detecting molecular-genetic information.

In addition the invention provides a medical therapy apparatus, in particular a cardiac pacemaker or a defibrillator, which has a sensor of that kind.

The advantages of the invention are in particular that detection of molecular-genetic information means that a further parameter is available, for controlling a medical therapy apparatus. A sensor of that kind, which like the therapy apparatus itself can be disposed inside or outside the body, can thus advantageously detect for example genetic defects which result in a change in the stimulation threshold in the case of pacemakers. In that way a medical therapy apparatus which is so equipped can also adapt the stimulation threshold to particularities of that kind which permanently prevail in the respective organism. The sensors according to the invention can be part of a therapy apparatus, in module-like fashion, so that they can be interchanged at any time or can also be subsequently added. The sensors according to the invention can however also be a fixed integral component part of a medical therapy apparatus.

Furthermore, by virtue of the invention, it is advantageously possible also to determine genetic or biological indicators, besides clinical indicators for cardiac disrhythmia phenomena or other malfunctions of the organism. In that way, by virtue of the invention, for example particular susceptibility on the part of the organism to cardiac disrhythmias or also for given kinds of cardiac disrhythmias can be determined or detected at an early stage. If such a sensor according to the invention is then part of a medical therapy apparatus, then having regard to such a genetic parameter it is possible to determine an indicator signal as a measurement in respect of an imminent event which is in need of therapy. Certain physiological states of the organism, which require treatment, can thus already be detected at the outset and thus the use of suitable therapy measures on the part of the therapy apparatus can be initiated or prepared.

In an advantageous embodiment of the invention the sensor element has at least one docking element, to which docking element molecules of the organism can be docked, wherein the docking specificity of the docking element is known. It is thus possible by means of such a docking element to ascertain whether given molecules are present in the organism. If in that respect the docking specificity of the docking element is for example so set that certain genetic defects which manifest themselves in certain molecules, of a specific configuration, in the organism, can be detected in that manner, then the sensor can detect that genetic effect and possibly signal same to a therapy apparatus. The therapy apparatus can then in turn—possibly after setting or enablement by the doctor—again initiate a suitable therapy measure or adapt the strength of the therapy measure to the detected genetic defect. In the case of cardiac pacemakers, in this connection the stimulation threshold can be raised or lowered according to the known effects of the detected genetic defect.

In order to detect the above-mentioned known molecules, the docking element itself can include a known molecule. Those known molecules are preferably synthetic oligonucleotides or PCR-generated cDNA fragments. By means of such oligonucleotides or cDNA it is possible to bind complementary DNA pieces of the organism to be investigated. As the oligonucleotides or cDNA fragments serving as docking elements are known, that means that the bound DNA piece is also known. The presence of a given DNA piece then makes it possible to infer back to a given state of the organism or a morbid change in the organism. In that way for example it is also possible to ascertain the presence or the amount of given enzymes in the organism. That can be helpful in terms of early detection of a cardiac infarct.

In a further preferred embodiment the sensor elements are preferably provided at least twice on the sensor. In that way random bindings of molecules to the docking elements can be recognised as being random and excluded in regard to evaluation of the measurement result.

In a particularly preferred feature the sensor according to the invention includes measuring elements which are preferably connected to each sensor element, which measuring elements detect hybridisation of a complementary molecule of the organism to the known molecule serving as the docking element. The measuring elements in that respect may be a current measuring element for measuring an electrical current produced by the hybridisation procedure, a fluorescence measuring element for detecting a fluorescence which is present due to hybridisation, a charge measuring element for detecting an electrical charge distribution altered by hybridisation, or a radiation measuring element for detecting radioactive radiation present due to hybridisation. If for example the arrangement involves a measuring element for detecting fluorescence, the DNA or RNA to be investigated in the organism is suitably provided with fluorescence markings. If a DNA or RNA marked in that way is hybridised with the complementary sequences on the sensor, that fluorescence and thus the hybridisation can be detected with the fluorescence measuring element.

In a particularly preferred embodiment of the present invention the known molecules serving as docking elements are arranged in a plurality of rows in mutually juxtaposed relationship in a chessboard-like configuration. Then, oligonucleotides or cDNA fragments which are characteristic of a given genetic defect or a given molecular-genetic state are arranged on that sensor which is provided with the sensor elements in a chessboard-like configuration, in a given sequence or a given pattern. In regard to that pattern, it is in turn known in what fashion, with a known genetic defect, the DNA or RNA of the organism which has that genetic defect binds to the molecules arranged in the chessboard-like configuration. Thus, a given binding or hybridisation pattern is known for a given gene or a given genetic defect. That hybridisation pattern can be stored for example in a storage means or memory of the sensor. If the sensor is then used to investigate an organism, the pattern which is then actually present can be detected by means of the measuring element and compared by means of a comparison device to the stored hybridisation patterns. If then the comparison device establishes identity of the current hybridisation pattern with a stored hybridisation pattern, the sensor is thus capable of ascertaining the presence of a given genetic defect or also a given molecular-genetic state of the organism being investigated. In that respect, it is also possible to ascertain the variation in respect of time of the hybridisation pattern. In that way it is possible for example to understand the expression of given genes. Such a measured expression of given genes in turn makes it possible to draw conclusions about a given state of the organism. If for example it is ascertained by means of the sensor according to the invention that given genes are expressed in the organism, which are expressed only in a given morbidly changed state of the organism, the sensor can then produce a corresponding signal which signals for example to a medical therapy apparatus the genetic defect of the organism or the morbidly changed expression of given genes. The morbidly increased production of given enzymes can also be ascertained in that way.

The above-mentioned known molecules are preferably arranged on a support substrate of glass, gel-coated glass, nylon, silicate, silicon or gallium arsenide. Suitable measuring elements are then preferably connected to the support substrate. In that respect, it is particularly preferred in accordance with the invention if the measuring elements are measuring elements for measuring an electrical current. In that way, the idea of the invention can be implemented in a particularly simple fashion insofar as an electrical current or a change in the electrical current when hybridisation has occurred with a molecule is measured at each sensor element.

In a further preferred embodiment, arranged on the chessboard-like sensor are cDNA fragments which are characteristic in respect of the expression of genes for given hormones. In that way, by means of the sensor according to the invention, it is also possible to record the hormone balance of the organism being monitored, in particular the presence or excess of a given hormone. Particularly if the medical therapy apparatuses of the invention involve cardiac pacemakers or defibrillators, it is of great importance to be able to detect given hormones in the body at an early stage. For, in particular the stimulation threshold for a cardiac pacemaker is inter alia dependent on a given hormone level in the organism. Then, in the case of such a cardiac pacemaker which is equipped with a sensor according to the invention, the pacemaker can be used in optimised fashion in terms of its function, by virtue of molecular-genetic detection of the hormone level by means of the sensor according to the invention.

It is also advantageous if the sensor element according to the invention or the medical therapy apparatus, in particular a medical therapy apparatus for the electrostimulation or other treatment of the heart, is provided with a sensor means at the input side, for producing at least one input signal which as an indicator signal forms a measurement in respect of a therapy threshold or a necessary level of therapy intensity. In that way the therapy threshold or intensity can be automatically set to the genetic predisposition of the patient.

It is particularly advantageous if, in the case of an electromedical apparatus which is adapted to be implantable, the indicator signal at least indirectly forms an input signal for a programming device which serves at least indirectly for setting at least one therapy or operating state parameter of the therapy apparatus. In that way the therapy apparatus can already be individually (pre-)set for a given patient upon manufacture or immediately after implantation. In this respect a corresponding production process for a medical therapy apparatus is also subject-matter of the invention.

In a preferred embodiment of a medical therapy apparatus of that kind, an addressing signal can be produced for a storage means or memory by means of the at least one indicator signal, which addressing signal in the manner of an addressable table (look-up table) contains in respective various storage regions which can be selected by the addressing signal in dependence on the indicator signal items of therapy information which can be read out as output signals and which are associated with the respective indicator signal.

Further preferred embodiments of the invention are set forth in the appendant claims.

Figure 2:
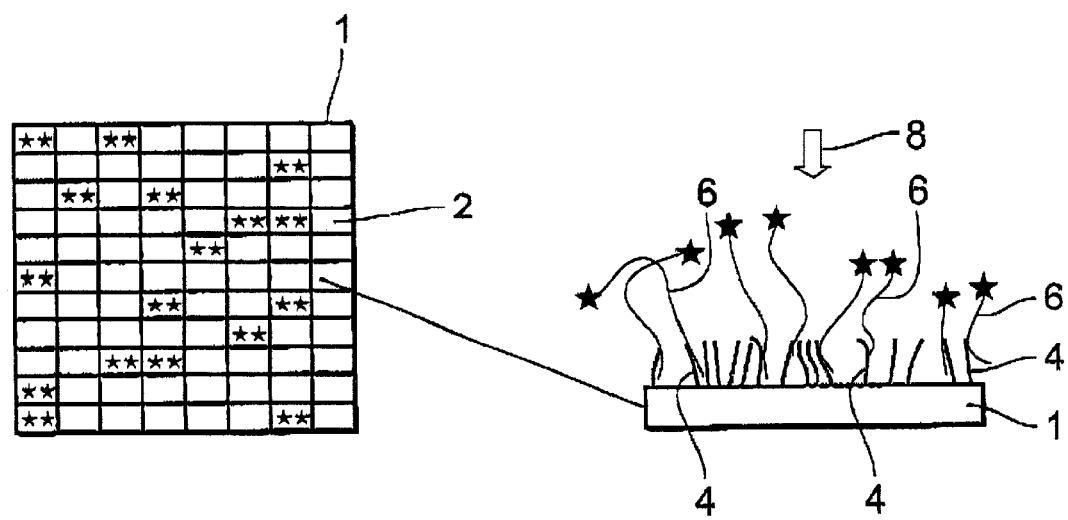
Figure 3:
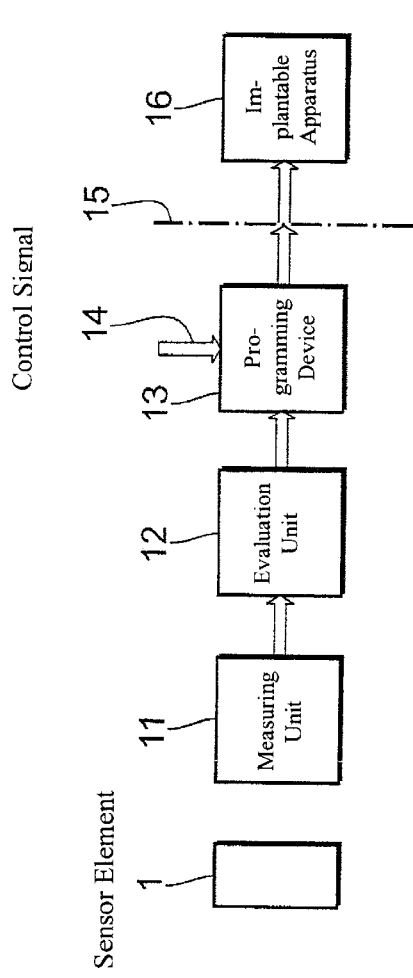
Figure 4:
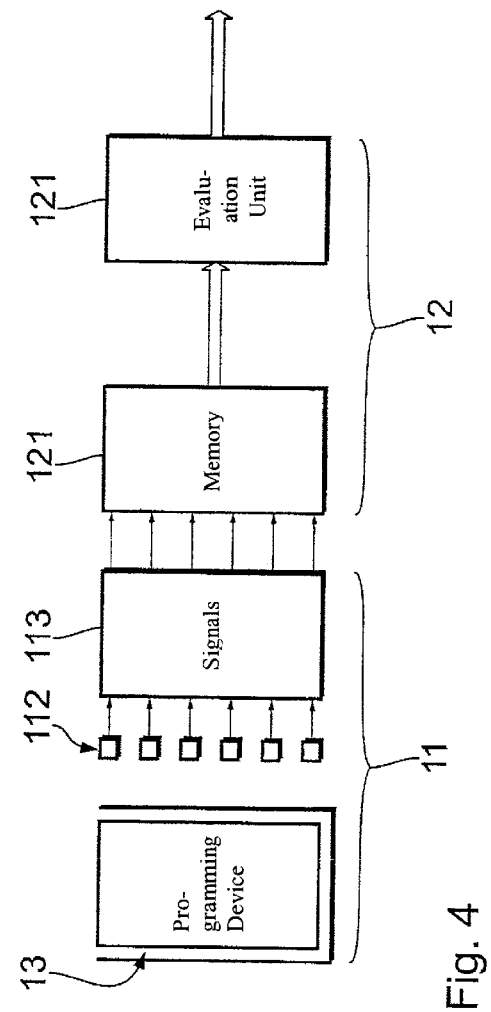

A preferred embodiment of the invention will now be described with reference to the drawing in which:

FIG. 1 is a diagrammatic plan view and a diagrammatic side view of a sensor according to the invention, FIG. 2 shows the sensor of FIG. 1 after binding of molecules to the sensor, FIG. 3 is a block diagram showing the principle of an embodiment in which the output signals of a sensor according to the invention are employed for programming a therapy apparatus, and FIG. 4 is a detail view relating to various blocks of the structure shown in FIG. 3.

FIG. 1 shows a plan view of a sensor 1, in the part shown at the left in the Figure. The sensor 1 is of a substantially square configuration in plan and carries 88 sensor elements 2 arranged in a chessboard-like configuration on that square surface.

The part of FIG. 1 shown at the right illustrates a side view of the sensor 1. In this case, a series of sensor elements 2 is clearly diagrammatically shown in the side view. Each of the sensor elements 2 carries two cDNA fragments 4 serving as docking elements according to the invention. Those cDNA fragments 4 are identical in respective pairs. The sequence of each cDNA fragment is specific for a given selected gene.

If now the sensor 1 is brought into contact with DNA or RNA 6 isolated from cells or tissue of the organism to be investigated, as symbolically indicated by the arrows 8, given portions of the isolated DNA or RNA now bind to given cDNA fragments 4 on the sensor 1. That binding of the DNA or RNA 6 to the cDNA fragments 4 is shown in the part of FIG. 2, which is illustrated at the right therein. Due to hybridisation of the complementary sequences of the isolated DNA or RNA 6 of the organism to the known cDNA fragments 4 of the individual sensor elements 2, a characteristic hybridisation pattern occurs on the sensor 1. That hybridisation pattern is diagrammatically shown in the part of FIG. 2, which is illustrated at the left. The hybridisation pattern becomes visible by the DNA or RNA 6 to be investigated having been previously marked with a fluorescence marker 10. The fluorescence marker 10 is illustrated in the Figures in the form of small stars at the end of the isolated DNA or RNA 6 respectively. The fluorescence of the fluorescence markers 10 can be detected by means of suitable scanners (not shown) serving as measuring elements according to the invention. In that way it is possible to ascertain the hybridisation pattern in the left-hand part of FIG. 2, on the basis of the fluorescence markers 10.

The hybridisation pattern ascertained in that way can then be compared to a known stock of hybridisation patterns stored in a storage means or memory. If then identity is detected with a hybridisation pattern stored in the storage means, the sensor 1 can thus establish the presence or the expression of a given gene in the organism being investigated and possibly signal same to a therapy apparatus connected thereto. Detection of the hybridisation pattern which is characteristic in respect of a given gene, hormone or enzyme can be implemented automatically in a medical therapy apparatus, insofar as a DNA or RNA 6 of the organism is automatically isolated by the sensor 1 and automatically brought into contact with the cDNA fragments 4, in which case finally hybridisation of the DNA or RNA 6 to given cDNA fragments 4 is automatically ascertained by means of the measuring elements.

FIGS. 3 and 4 show an embodiment of the invention with an evaluation unit for the sensor element together with a programmable therapy apparatus in the form of an implantable cardiac stimulation and/or defibrillation apparatus, in each case in the form of a block circuit diagram.

The arrangement shown in FIG. 3 has a measuring unit 11 which includes at least one measuring element for evaluation of a sensor element. The sensor element 1 which is brought into contact with a genetic sample from the patient is evaluated in the measuring unit by a procedure wherein—as described above—an output signal pattern, which contains the genetic information, of the sensor element in question is interrogated and fed to an evaluation unit 12. In the evaluation unit 12, the output signal pattern of the sensor element is converted into an input signal for a storage means or memory which—in suitably encoded form—contains various therapy instructions in dependence on predetermined genetic predispositions. The illustrated apparatus involves instructions concerning patient electrotherapy. Accordingly, in dependence on the respective output signal pattern, a control signal is produced for a programming device 13, which influences the implantable stimulation or defibrillation apparatus 15 together with further programming control signals 14 which can be directly inputted by the doctor, when it is brought into communication relationship with the therapy apparatus.

While therefore hitherto setting of a medical therapy apparatus depended entirely on the medical diagnosis by the doctor, now the parameters to be programmed can be influenced—at least additionally—directly by the genetic predisposition of the patient. Thus for example the therapy threshold or the necessary level of therapy intensity for each patient can be dependent on hereditary characteristics, which forms a therapy constant for the patient in question. That therapy constant is derived as a one-off operation by the described genetic investigation of the patient and incorporated into the programming of the electrotherapy for the patient so that treatment of the patient is better adapted to the individual needs of the patient.

FIG. 4 shows once again in detail the measuring unit 11 and the evaluation unit 12. The sensor element 1 which has been previously brought into reaction contact with genetic material of the patient is inserted into the receiving portion 111 of the measuring unit 11. The inner part of the measuring unit 11 is provided with measuring elements 112 which receive signals which are delivered by the sensor element 1, possibly under suitable activation conditions. Those activation conditions involve for example light 113 if the sensor elements have fluorescing properties or a chemical activator if the relevant signals are produced by a chemo-optical process. The output signals of the measuring elements pass into respectively associated intermediate storage means or memories (not shown) which retain the respective signal states for further evaluation, even if the process which triggers the signal in question is already concluded. Storage is preceded by a digitisation step which is implemented in the simplest case (one-stage) by a Schmitt trigger or however (multistage) by an analog-digital converter unit.

The digital output signals of the measuring elements pass as indicator signals by way of an interface 114 into an addressable storage means or memory 121 of the downstream-connected evaluation unit 122 where they are retained for further processing. The output signals form in digitised form a signal pattern which is used for addressing of the addressable storage means or memory, in such a form that said memory forms a look-up table which for each input signal or each relevant combination of input signals delivers an output signal which characterises a therapy setting or an auxiliary signal for a therapy setting for the therapy apparatus to be programmed. This involves for example a measuring signal for a therapy threshold which is characteristic of the patient in question or a characteristic level of therapy intensity corresponding to the genetic predisposition of the patient.

The output signals in question are passed by way of a downstream-connected output unit 12 to the programming apparatus (shown in FIG. 3 in the form of a block) where, alone or in combination with a therapy parameter set by the doctor (arrow 14) they form control signals for influencing the implantable therapy apparatus. As the genetic predisposition of the patient is to be viewed as being essentially invariable, the illustrated measures need to be carried out only once for each patient—preferably already prior to or immediately after implantation of the medical apparatus.

In the case of use directly upon manufacture, there is no necessity for the programming apparatus to form a separate unit. Here, the input of the corresponding therapy parameters, which was derived from the at least one indicator signal, is advantageously used directly for producing a programmable memory (EPROM etc) which contains the therapy parameters of the apparatus to be produced. That can in fact be effected in a manufacturing step at a stage which is still prior to assembly or configuring of the medical apparatus in question, so that, in the case of on-demand production, it is possible to produce apparatuses which are individually tailored to the needs of individual patients. In that respect the indicator data of the sensor do not need to be ascertained directly in the production premises of the apparatus but can be detected at the patient and transmitted to the production premises by way of suitable communication means. In that way the apparatus no longer needs to be modified later.

What is claimed is:

1. A sensor for obtaining information about the state of an organism for a medical therapy apparatus, comprising:
    at least two sensor elements for detecting molecular-genetic information, each said sensor element comprising at least one docking element, each said docking element having a known specificity for molecules of the organism and including a known molecule, and
    at least one measuring element, connected to a predominant number of the said at least two sensor elements, said at least one measuring element detecting hybridisation of a complementary molecule of the organism to the known molecule, each said measuring element being selected from a group consisting of: an element for measuring an electrical current produced by hybridisation, an element for detecting fluorescence present due to hybridisation, an element for detecting an electrical charge distribution which is altered by hybridisation, and an element for detecting a radioactive radiation present due to hybridisation,
    wherein the known molecules are selected from a group consisting of: synthetic oligonucleotides and PCR-generated cDNA fragments, and
    wherein at least one of said at least two sensor elements is present in identical form at least twice on the sensor.

2. The sensor as set forth in claim 1, comprising:
    a means for the storage of hybridisation associations for the known molecules and a means for comparison of the detected hybridisation to a standard stored in the storage means, said comparison means connected to one of said at least one measuring element.

3. The sensor as set forth in claim 2 comprising:
    a means for storing the progression in respect of time of hybridisation to known molecules, wherein the comparison means are adapted to compare a progression in respect of time of hybridisation, which is detected by means of one of the said at least one measuring element, to the stored progression.

4. The sensor of claim 3 comprising:
    a means for storing hybridisation patterns of hybridisations to known molecules, wherein the comparison means are adapted to compare a hybridisation pattern which is detected by means of one of the said at least one measuring element to a stored hybridisation pattern.

5. The sensor of claim 4 wherein said at least two sensor elements are arranged in a row.

6. The sensor as set forth in claim 5 wherein a plurality of rows of approximately equal length are arranged in mutually juxtaposed relationship in a chessboard-like configuration on the sensor.

7. The sensor of claim 6 comprising a support substrate for said at least two sensor elements, the sensor elements being immobilised thereon.

8. The sensor as set forth in claim 7 wherein the support substrate is selected from a group consisting of: glass, gel-coated glass, nylon, silicate, silicon and gallium arsenide.

9. The sensor of claim 1, wherein there are at least one hundred of the said at least two sensor elements.

10. A medical therapy apparatus, comprising:
    a sensor means comprising at least one sensor element for detecting molecular genetic information;
    at least one therapy application means; and
    at least one linking and/or processing means connected between the sensor means at an input side and said at least one therapy application means at an output side.

11. The medical therapy apparatus of claim 10, wherein one of said at least one therapy application means is for the electrostimulation of the heart.

12. A medical therapy apparatus, comprising
    at least one sensor means at the input side for producing at least one input signal,
    at least one linking and/or processing stage for processing the input signal to afford an indicator signal, which indicator signal forms a measurement for a probably imminent event requiring therapy or a therapy outcome, and
    at least one therapy application means at the output side, which is controlled by the indicator signal, wherein the input signal and/or one of the input signals is an item of molecular-genetic information acquired by means of a sensor as set forth in one of claims 1 and 2 through 9.

13. A medical therapy apparatus, comprising:
    a sensor means at an input side thereof for producing at least one input signal,
    at least one linking and/or processing stage for processing the input signal to afford an indicator signal, which indicator signal forms a measurement in respect of a therapy threshold or a necessary level of therapy intensity, and
    at least one therapy application means at an output side, which is controlled by the indicator signal, wherein the at least one input signal is an item of medical information acquired by means of a sensor as set forth in one of claims 1 and 2 through 9.

14. The medical therapy apparatus of claim 13 wherein the apparatus is implantable and wherein the indicator signal at least indirectly forms an input signal for a programming device that at least indirectly sets at least one therapy or operating state parameter of the therapy apparatus in the implanted state or already upon manufacture thereof, and a corresponding process.

15. The medical therapy apparatus of claim 14 wherein an addressing signal is produced for a storage means by means of the at least one indicator signal, which in the manner of an addressable look-up table respectively contains in various storage regions which can be selected by the addressing signal in dependence on the indicator signal items of therapy information which can be read out as output signals and which are associated with the respective indicator signal.

* * * * *